United States Patent
Emett et al.

(10) Patent No.: US 9,796,645 B2
(45) Date of Patent: Oct. 24, 2017

(54) POLY ALPHA OLEFIN COMPOSITIONS

(75) Inventors: Craig J. Emett, Houston, TX (US); Mark P. Hagemeister, Houston, TX (US); Wenning W. Han, Houston, TX (US); Bruce A. Harrington, Houston, TX (US); Phillip T. Matsunaga, Houston, TX (US); Charles J. Ruff, Houston, TX (US); Kevin B. Stavens, Houston, TX (US); Margaret M. Wu, Skillman, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 875 days.

(21) Appl. No.: 13/612,246

(22) Filed: Sep. 12, 2012

(65) Prior Publication Data

US 2013/0245343 A1    Sep. 19, 2013

Related U.S. Application Data

(63) Continuation-in-part of application No. 11/995,118, filed as application No. PCT/US2006/021231 on Jun. 2, 2006, now Pat. No. 8,748,361.

(60) Provisional application No. 61/545,386, filed on Oct. 10, 2011, provisional application No. 61/545,393, filed on Oct. 10, 2011, provisional application No. 60/700,600, filed on Jul. 19, 2005.

(51) Int. Cl.
| | |
|---|---|
| C10L 1/16 | (2006.01) |
| C07C 11/02 | (2006.01) |
| C08F 210/04 | (2006.01) |
| C08F 210/14 | (2006.01) |
| C08F 10/14 | (2006.01) |
| C08F 110/14 | (2006.01) |
| C08F 4/659 | (2006.01) |
| C08F 4/6592 | (2006.01) |

(52) U.S. Cl.
CPC ............ *C07C 11/02* (2013.01); *C08F 10/14* (2013.01); *C08F 210/04* (2013.01); *C08F 210/14* (2013.01); *C08F 4/65908* (2013.01); *C08F 4/65912* (2013.01); *C08F 4/65925* (2013.01); *C08F 4/65927* (2013.01); *C08F 110/14* (2013.01)

(58) Field of Classification Search
CPC  C08F 110/14; C08F 2500/02; C08F 2500/03; C08F 2500/17; C08F 2500/20; C08F 10/14; C08F 10/04; C08F 210/14; C08F 4/65908; C08F 4/65927; C07C 11/02
USPC .................. 508/517, 521, 523, 524, 591
See application file for complete search history.

(56) References Cited

U.S. PATENT DOCUMENTS

| | | | |
|---|---|---|---|
| 2,978,442 | A | 4/1961 | Brightbill et al. |
| 3,164,578 | A | 1/1965 | Baker et al. |
| 3,883,417 | A | 5/1975 | Woo et al. |
| 4,016,349 | A | 4/1977 | McKenna |
| 4,132,663 | A | 1/1979 | Heilman et al. |
| 4,149,178 | A | 4/1979 | Estes |
| 4,172,855 | A | 10/1979 | Shubkin et al. |
| 4,180,575 | A | 12/1979 | Rochling et al. |
| 4,239,930 | A | 12/1980 | Allphin et al. |
| 4,263,465 | A | 4/1981 | Sheng et al. |
| 4,263,712 | A | 4/1981 | Schroder |
| 4,451,684 | A | 5/1984 | Pasky |
| 4,469,912 | A | 9/1984 | Blewett et al. |
| 4,587,368 | A | 5/1986 | Pratt |
| 4,701,489 | A | 10/1987 | Hughes et al. |
| 4,704,491 | A | 11/1987 | Tsutsui et al. |
| 4,892,851 | A | 1/1990 | Ewen et al. |
| 4,950,822 | A | 8/1990 | Dileo et al. |
| 4,962,262 | A | 10/1990 | Winter et al. |
| 4,973,788 | A | 11/1990 | Lin et al. |
| 4,990,709 | A | 2/1991 | Wu |
| 4,990,771 | A | 2/1991 | Minoura et al. |
| 5,017,299 | A | 5/1991 | Gutierrez et al. |

(Continued)

FOREIGN PATENT DOCUMENTS

| | | |
|---|---|---|
| EP | 0426638 | 10/1990 |
| WO | 97/22635 | 6/1997 |

(Continued)

OTHER PUBLICATIONS

A. Onopchenko, "*BF3-Catalyzed Oligomerization of Alkenes: Structures, Mechanisms, and Properties*", Ind. Eng. Chem. Prod. Res. Dev., 1983, vol. 22, pp. 182-191.

(Continued)

*Primary Examiner* — Latosha Hines
(74) *Attorney, Agent, or Firm* — Nancy T. Waldrip; Siwen Chen

(57) ABSTRACT

This invention is directed to a poly alpha olefin (PAO) composition formed in a first oligomerization, wherein at least portions of the PAO have properties that make them highly desirable for a subsequent oligomerization. A preferred process for producing this PAO uses a single site catalyst at high temperatures without adding hydrogen to produce a low viscosity PAO with excellent Noack volatility at high conversion rates. This PAO comprises a dimer product with at least 25 wt % tri-substituted vinylene olefins wherein said dimer product is highly desirable as a feedstock for a subsequent oligomerization. This PAO also comprises trimer and optionally higher oligomer products with outstanding properties that make these products useful as lubricant basestocks following hydrogenation.

17 Claims, No Drawings

(56) References Cited

U.S. PATENT DOCUMENTS

| | | |
|---|---|---|
| 5,087,788 A | 2/1992 | Wu |
| 5,186,851 A | 2/1993 | Gutierrez et al. |
| 5,188,724 A | 2/1993 | Heilman et al. |
| 5,220,100 A | 6/1993 | Massie et al. |
| 5,241,025 A | 8/1993 | Hlatky et al. |
| 5,264,642 A | 11/1993 | Wu |
| 5,284,988 A * | 2/1994 | Schaerl et al. .............. 585/525 |
| 5,369,196 A | 11/1994 | Matsumoto et al. |
| 5,382,739 A | 1/1995 | Atkins et al. |
| 5,447,895 A | 9/1995 | Marks et al. |
| 5,462,995 A | 10/1995 | Hosaka et al. |
| 5,498,815 A | 3/1996 | Schaerfl, Jr. et al. |
| 5,552,504 A | 9/1996 | Bennett et al. |
| 5,554,310 A | 9/1996 | Rossi et al. |
| 5,637,400 A | 6/1997 | Brekner et al. |
| 5,679,812 A | 10/1997 | Winter et al. |
| 5,688,887 A | 11/1997 | Bagheri et al. |
| 5,690,832 A | 11/1997 | Tavlarides et al. |
| 5,731,254 A | 3/1998 | Winter et al. |
| 5,846,896 A | 12/1998 | Ewen |
| 5,852,143 A | 12/1998 | Sishta et al. |
| 5,859,159 A | 1/1999 | Rossi et al. |
| 6,043,401 A | 3/2000 | Bagheri et al. |
| 6,133,209 A | 10/2000 | Rath et al. |
| 6,147,271 A | 11/2000 | Strebel et al. |
| 6,388,032 B1 | 5/2002 | Yamaura et al. |
| 6,414,090 B2 | 7/2002 | Minami et al. |
| 6,414,091 B2 | 7/2002 | Moritomi et al. |
| 6,479,722 B1 | 11/2002 | De Wet et al. |
| 6,541,584 B1 | 4/2003 | Resconi |
| 6,548,723 B2 | 4/2003 | Bagheri et al. |
| 6,548,724 B2 | 4/2003 | Bagheri et al. |
| 6,642,169 B2 | 11/2003 | Weatherhead |
| 6,646,174 B2 | 11/2003 | Clarembeau |
| 6,706,828 B2 | 3/2004 | DiMaio |
| 6,713,438 B1 | 3/2004 | Baillargeon et al. |
| 6,824,671 B2 | 11/2004 | Goze et al. |
| 6,858,767 B1 | 2/2005 | DiMaio et al. |
| 6,960,700 B1 | 11/2005 | Sethna et al. |
| 7,060,768 B2 | 6/2006 | Brookhart et al. |
| 7,129,197 B2 | 10/2006 | Song et al. |
| 7,473,815 B2 | 1/2009 | Lambert et al. |
| 7,511,104 B2 | 3/2009 | Pehlert et al. |
| 7,544,850 B2 | 6/2009 | Goze et al. |
| 7,547,811 B2 | 6/2009 | Kramer et al. |
| 7,592,497 B2 | 9/2009 | Yang et al. |
| 7,601,256 B2 | 10/2009 | Beall |
| 8,455,416 B2 | 6/2013 | Bagheri et al. |
| 2001/0041817 A1 | 11/2001 | Bagheri et al. |
| 2001/0041818 A1 | 11/2001 | Bagheri et al. |
| 2003/0055184 A1* | 3/2003 | Song et al. .............. 526/160 |
| 2004/0022508 A1 | 2/2004 | Belardi et al. |
| 2004/0033908 A1 | 2/2004 | Deckman et al. |
| 2004/0087746 A1 | 5/2004 | Razavi |
| 2004/0097772 A1 | 5/2004 | Deckers et al. |
| 2004/0147693 A1 | 7/2004 | DiMaio |
| 2004/0220359 A1 | 11/2004 | Abhari et al. |
| 2004/0230016 A1 | 11/2004 | Blackbrow et al. |
| 2005/0059563 A1 | 3/2005 | Sullivan et al. |
| 2005/0101761 A1 | 5/2005 | Lambert et al. |
| 2005/0183988 A1 | 8/2005 | Freerks et al. |
| 2007/0000807 A1 | 1/2007 | Wu et al. |
| 2007/0011832 A1 | 1/2007 | Keidel et al. |
| 2007/0043248 A1 | 2/2007 | Wu et al. |
| 2007/0208151 A1 | 9/2007 | Okada et al. |
| 2008/0146469 A1 | 6/2008 | Sato et al. |
| 2009/0005279 A1 | 1/2009 | Wu et al. |
| 2009/0156874 A1 | 6/2009 | Patil et al. |
| 2009/0221775 A1 | 9/2009 | Hagemeister et al. |
| 2009/0240012 A1 | 9/2009 | Patil et al. |
| 2009/0281360 A1 | 11/2009 | Knowles et al. |
| 2010/0029242 A1 | 2/2010 | Orr et al. |
| 2010/0069687 A1 | 3/2010 | Kosover et al. |
| 2010/0077842 A1 | 4/2010 | Rosenbaum et al. |
| 2011/0039743 A1 | 2/2011 | Bagheri et al. |

FOREIGN PATENT DOCUMENTS

| | | |
|---|---|---|
| WO | WO 0132590 A2 * | 5/2001 |
| WO | WO 02092729 A1 * | 11/2002 |
| WO | 03/020856 | 3/2003 |
| WO | WO 2007/011832 | 1/2007 |
| WO | WO 2008/010865 | 1/2008 |
| WO | WO 2009/017953 | 2/2009 |
| WO | WO 2009/123800 | 10/2009 |
| WO | 2010/036331 | 4/2010 |
| WO | 2011/079042 | 6/2011 |

OTHER PUBLICATIONS

Patt, S.L.; Shoolery, N., J.Mag.Reson., 46:535(1982).
Doddrell, D.M.; Pegg, D.T., Bendall, M. R., J. Mag. Reson., 48:323 (1982).

* cited by examiner

US 9,796,645 B2

POLY ALPHA OLEFIN COMPOSITIONS

PRIORITY CLAIM

This application claims priority to U.S. Application 61/545,386 which was filed Oct. 10, 2011 and U.S. Application 61/545,393 which was filed Oct. 10, 2011. This application also claims priority to, and is a continuation in part of, U.S. application Ser. No. 11/995,118, filed on May 28, 2008, now U.S. Pat. No. 8,748,361 published as US 2009-005279, which claims priority to PCT/US2006/021231, filed Jun. 2, 2006, published as WO2007/001459, and which claims priority to U.S. Provisional Application 60/700,600, filed Jul. 19, 2005.

FIELD OF THE INVENTION

This disclosure relates to improved low viscosity poly alpha olefin (PAO) compositions useful as lubricant basestocks.

BACKGROUND OF THE INVENTION

Efforts to improve the performance of lubricant basestocks by the oligomerization of hydrocarbon fluids have been ongoing in the petroleum industry for over fifty years. These efforts have led to the market introduction of a number of synthetic lubricant basestocks. Much of the research involving synthetics has been toward developing fluids that exhibit useful viscosities over a wide temperature range while also maintaining lubricities, thermal and oxidative stabilities, and pour points equal to or better than those for mineral lubricants.

The viscosity-temperature relationship of a lubricant is one critical criteria that must be considered when selecting a lubricant for a particular application. The viscosity index (VI) is an empirical number which indicates the rate of change in the viscosity of an oil within a given temperature range. A high VI oil will thin out at elevated temperatures slower than a low VI oil. In most lubricant applications, a high VI oil is desirable because maintaining a higher viscosity at higher temperatures translates into better lubrication.

PAOs have been recognized for over 30 years as a class of materials that are exceptionally useful as high performance synthetic lubricant basestocks. They possess excellent flow properties at low temperatures, good thermal and oxidative stability, low evaporation losses at high temperatures, high viscosity index, good friction behavior, good hydrolytic stability, and good erosion resistance. PAOs are miscible with mineral oils, other synthetic hydrocarbon liquids, fluids and esters. Consequently, PAOs are suitable for use in engine oils, compressor oils, hydraulic oils, gear oils, greases and functional fluids.

PAOs may be produced by the use of Friedel-Craft catalysts, such as aluminum trichloride or boron trifluoride, and a protic promoter. The alpha olefins generally used as feedstock are those in the $C_6$ to $C_{20}$ range, most preferably 1-hexene, 1-octene, 1-nonene, 1-decene, 1-dodecene, and 1-tetradecene. In the current process to produce low viscosity PAOs using Friedel-Craft catalysts, the dimers portion is typically separated via distillation. This portion may be hydrogenated and sold for use as a lubricant basestock, however its value is low compared to other portions of the product stream due to its high volatility and poor low temperature properties.

The demand for high quality PAOs has been increasing for several years, driving research in alternatives to the Friedel-Craft process. Metallocene catalyst systems are one such alternative. Most of the metallocene-based focus has been on high-viscosity-index-PAOs (HVI-PAOs) and higher viscosity oils for industrial and commercial applications. Examples include U.S. Pat. No. 6,706,828, which discloses a process for producing PAOs from meso-forms of certain metallocene catalysts with methylalumoxane (MAO). Others have made various PAOs, such as polydecene, using various metallocene catalysts not typically known to produce polymers or oligomers with any specific tacticity. Examples include U.S. Pat. No. 5,688,887; U.S. Pat. No. 6,043,401; WO 2003/020856; U.S. Pat. No. 5,087,788; U.S. Pat. No. 6,414,090; U.S. Pat. No. 6,414,091; U.S. Pat. No. 4,704,491; U.S. Pat. No. 6,133,209; and U.S. Pat. No. 6,713,438. ExxonMobil Chemical Company has been active in the field and has several pending patent applications on processes using various bridged and unbridged metallocene catalysts. Examples include published applications WO 2007/011832; WO 2008/010865; WO 2009/017953; and WO 2009/123800.

Although most of the research on metallocene-based PAOs has focused on higher viscosity oils, recent research has looked at producing low viscosity PAOs for automotive applications. A current trend in the automotive industry is toward extending oil drain intervals and improving fuel economy. This trend is driving increasingly stringent performance requirements for lubricants. New PAOs with improved properties such as high viscosity index, low pour point, high shear stability, improved wear performance, increased thermal and oxidative stability, and/or wider viscosity ranges are needed to meet these new performance requirements. New methods to produce such PAOs are also needed. US 2007/0043248 discloses a process using a metallocene catalyst for the production of low viscosity (4 to 10 cSt) PAO basestocks. This technology is attractive because the metallocene-based low viscosity PAO has excellent lubricant properties.

One disadvantage of the low viscosity metallocene-catalyzed process is that a significant amount of dimer is formed. This dimer is not useful as a lubricant basestock because it has very poor low temperature and volatility properties. Recent industry research has looked at recycling the dimer portion formed in the metallocene-catalyzed process into a subsequent oligomerization process.

U.S. Pat. No. 6,548,724 discloses a multistep process for the production of a PAO in which the first step involves polymerization of a feedstock in the presence of a bulky ligand transition metal catalyst and a subsequent step involves the oligomerization of some portion of the product of the first step in the presence of an acid catalyst. The dimer product formed by the first step of U.S. Pat. No. 6,548,724 exhibits at least 50%, and preferably more than 80%, of terminal vinylidene content. The product of the subsequent step in U.S. Pat. No. 6,548,724 is a mixture of dimers, trimers, and higher oligomers, and yield of the trimer product is at least 65%.

U.S. Pat. No. 5,284,988 discloses a multistep process for the production of a PAO in which a vinylidene dimer is first isomerized to form a tri-substituted dimer. The tri-substituted dimer is then reacted with a vinyl olefin in the presence of an acid catalyst to form a co-dimer of said tri-substituted dimer and said vinyl olefin. U.S. Pat. No. 5,284,988 shows that using the tri-substituted dimer, instead of the vinylidene dimer, as a feedstock in the subsequent oligomerization step results in a higher selectivity said co-dimer and less formation of product having carbon members greater than or less than the sum of the carbon members of the vinylidene and alpha-olefin. As a result, the lubricant may be tailored to a specific viscosity at high yields, which is highly desirable due to lubricant industry trends and demands. The U.S. Pat. No. 5,284,988 process, however, requires the additional step of isomerization to get the tri-substituted dimer. Additionally, the reaction rates disclosed in U.S. Pat. No. 5,284,988 are very slow, requiring 2-20 days just to prepare the initial vinylidene dimer.

An additional example of a process involving the recycle of a dimer product is provided in US 2008/0146469 which discloses an intermediate comprised primarily of vinylidene.

SUMMARY OF THE INVENTION

Disclosed herein is a PAO formed in via oligomerization, wherein at least portions of this PAO have properties that make said portions highly desirable as feedstocks to a subsequent oligomerization. One preferred process for producing this invention uses a single site catalyst at high temperatures without adding hydrogen in the first oligomerization to produce a low viscosity PAO with excellent Noack volatility at high conversion rates. The PAO formed comprises a distribution of products, including dimers, trimers, and higher oligomers. This PAO or the respective dimer, trimer, and further oligomer portions may hereinafter be referred to as the "intermediate PAO," "intermediate PAO dimer," "intermediate PAO trimer," and the like. The term "intermediate PAO" and like terms are used in this disclosure only to differentiate PAOs formed in the first oligomerization from PAOs formed in any subsequent oligomerization, and said terms are not intended to have any meaning beyond being useful for making this differentiation. When the first oligomerization uses a metallocene based catalyst system, the resulting PAO may also be referred to as "intermediate mPAO", as well as portions thereof may be referred to as "intermediate mPAO dimer," "intermediate mPAO trimer," and the like.

The intermediate PAO comprises a tri-substituted vinylene dimer that is highly desirable as a feedstock for a subsequent oligomerization. This intermediate PAO also comprises trimer and optionally tetramer and higher oligomer portions with outstanding properties that make these portions useful as lubricant basestocks following hydrogenation. In an embodiment, the intermediate PAO dimer portion comprises greater than 25 wt % tri-substituted vinylene olefins. This intermediate PAO dimer comprising greater than 25 wt % tri-substituted vinylene olefins has properties that make it especially desirable for a subsequent recycle to a second oligomerization in the presence of an optional linear alpha olefin (LAO) feed comprising one or more $C_6$ to $C_{24}$ olefins, an oligomerization catalyst, and an activator. The structure, especially the olefin location, of this intermediate PAO dimer is such that, when recycled and reacted under such conditions, it reacts preferentially with the LAO, instead of reacting with other intermediate PAO dimer, to form a co-dimer at high yields. In the present invention, the term "co-dimer" is used to designate the reaction product of the intermediate PAO dimer with a linear alpha olefin (LAO) monomer.

DETAILED DESCRIPTION OF THE INVENTION

This invention is directed to a PAO composition formed in an oligomerization, wherein at least portions of the PAO have properties that make them highly desirable for a subsequent oligomerization. A preferred process for the first oligomerization uses a single site catalyst at high temperatures without adding hydrogen to produce a low viscosity PAO with excellent Noack volatility at high conversion rates. This PAO comprises a dimer product with at least 25 wt % tri-substituted vinylene olefins wherein said dimer product is highly desirable as a feedstock for a subsequent oligomerization. This PAO also comprises trimer and optionally tetramer and higher oligomer products with outstanding properties that make these products useful as lubricant basestocks following hydrogenation.

The PAOs formed in the invention are liquids. For the purposes of this invention, the term "liquid" is defined to be a fluid that has no distinct melting point above 0° C., preferably no distinct melting point above −20° C., and has a kinematic viscosity at 100° C. of 3000 cSt or less—though all of the liquid PAOs of the present invention have a kinematic viscosity at 100° C. of 20 cSt or less as further disclosed.

When used in the present invention, in accordance with conventional terminology in the art, the following terms are defined for the sake of clarity. The term "vinyl" is used to designate groups of formula $RCH=CH_2$. The term "vinylidene" is used to designate groups of formula $RR'=CH_2$. The term "disubstituted vinylene" is used to designate groups of formula $RCH=CHR'$. The term "tri-substituted vinylene" is used to designate groups of formula $RR'C=CHR''$. The term "tetrasubstituted vinylene" is used to designated groups of formula $RR'C=CR''R'''$. For all of these formulas, R, R', R", and R' are alkyl groups which may be identical or different from each other.

The monomer feed used in the oligomerization is typically comprised of monomers of 6 to 24 carbon atoms, usually 6 to 20, and preferably 6 to 14 carbon atoms, such as 1-hexene, 1-octene, 1-nonene, 1-decene, 1-dodecene, and 1-tetradecene. Olefins with even carbon numbers are preferred as are LAOs. Additionally, these olefins are preferably treated to remove catalyst poisons, such as peroxides, oxygen, sulfur, nitrogen-containing organic compounds, and/or acetylenic compounds as described in WO 2007/011973.

Catalyst

Useful catalysts in the oligomerization include single site catalysts. In a preferred embodiment, the first oligomerization uses a metallocene catalyst. In this disclosure, the terms "metallocene catalyst" and "transition metal compound" are used interchangeably. Preferred classes of catalysts give high catalyst productivity and result in low product viscosity and low molecular weight. Useful metallocene catalysts may be bridged or un-bridged and substituted or un-substituted. They may have leaving groups including dihalides or dialkyls. When the leaving groups are dihalides, tri-alkyl-aluminum may be used to promote the reaction. In general, useful transition metal compounds may be represented by the following formula:

wherein:

$M_1$ is an optional bridging element, preferably selected from silicon or carbon;

$M_2$ is a Group 4 metal;

Cp and Cp* are the same or different substituted or unsubstituted cyclopentadienyl ligand systems wherein, if substituted, the substitutions may be independent or linked to form multicyclic structures;

$X_1$ and $X_2$ are independently hydrogen, hydride radicals, hydrocarbyl radicals, substituted hydrocarbyl radicals, silylcarbyl radicals, substituted silylcarbyl radicals, germylcarbyl radicals, or substituted germylcarbyl radicals or are preferably independently selected from hydrogen, branched or unbranched $C_1$ to $C_{20}$ hydrocarbyl radicals, or branched or unbranched substituted $C_1$ to $C_{20}$ hydrocarbyl radicals; and $X_3$ and $X_4$ are independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both $X_3$ and $X_4$ are joined and bound to the metal atom to form a metallacycle ring containing from about 3 to about 20 carbon atoms, or are preferably independently selected from hydrogen, branched or unbranched $C_1$ to $C_{20}$ hydrocarbyl radicals, or branched or unbranched substituted $C_1$ to $C_{20}$ hydrocarbyl radicals.

For this disclosure, a hydrocarbyl radical is $C_1$-$C_{100}$ radical and may be linear, branched, or cyclic. A substituted hydrocarbyl radical includes halocarbyl radicals, substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated, or aromatic cyclic or polycyclic ring structure.

Halocarbyl radicals are radicals in which one or more hydrocarbyl hydrogen atoms have been substituted with at least one halogen (e.g., F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

In an embodiment, the transition metal compound may be represented by the following formula:

$X_1X_2M_1(CpCp^*)M_2X_3X_4$ wherein:

$M_1$ is a bridging element, and preferably silicon;

$M_2$ is a Group 4 metal, and preferably titanium, zirconium or hafnium;

Cp and Cp* are the same or different substituted or unsubstituted indenyl or tetrahydroindenyl rings that are each bonded to both $M_1$ and $M_2$;

$X_1$ and $X_2$ are independently hydrogen, hydride radicals, hydrocarbyl radicals, substituted hydrocarbyl radicals, silylcarbyl radicals, substituted silylcarbyl radicals, germylcarbyl radicals, or substituted germylcarbyl radicals; and $X_3$ and $X_4$ are independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both $X_3$ and $X_4$ are joined and bound to the metal atom to form a metallacycle ring containing from about 3 to about 20 carbon atoms.

In using the terms "substituted or unsubstituted tetrahydroindenyl," "substituted or unsubstituted tetrahydroindenyl ligand," and the like, the substitution to the aforementioned ligand may be hydrocarbyl, substituted hydrocarbyl, halocarbyl, substituted halocarbyl, silylcarbyl, or germylcarbyl. The substitution may also be within the ring giving heteroindenyl ligands or heterotetrahydroindenyl ligands, either of which can additionally be substituted or unsubstituted.

In another embodiment, useful transition metal compounds may be represented by the following formula:

$L^A L^B L^C_i MDE$ wherein:

$L^A$ is a substituted cyclopentadienyl or heterocyclopentadienyl ancillary ligand π-bonded to M;

$L^B$ is a member of the class of ancillary ligands defined for $L^A$, or is J, a heteroatom ancillary ligand σ-bonded to M; the $L^A$ and $L^B$ ligands may be covalently bridged together through a Group 14 element linking group;

$L^C_i$ is an optional neutral, non-oxidizing ligand having a dative bond to M (i equals 0 to 3);

M is a Group 4 or 5 transition metal; and

D and E are independently monoanionic labile ligands, each having a π-bond to M, optionally bridged to each other or $L^A$ or $L^B$. The mono-anionic ligands are displaceable by a suitable activator to permit insertion of a polymerizable monomer or a macromonomer can insert for coordination polymerization on the vacant coordination site of the transition metal compound.

One embodiment of this invention uses a highly active metallocene catalyst. In this embodiment, the catalyst productivity is greater than $$15,000 \frac{g_{PAO}}{g_{catalyst}},$$

preferably greater than $$20,000 \frac{g_{PAO}}{g_{catalyst}},$$

preferably greater than $$25,000 \frac{g_{PAO}}{g_{catalyst}},$$

and more preferably greater than $$30,000 \frac{g_{PAO}}{g_{catalyst}},$$

wherein $$\frac{g_{PAO}}{g_{catalyst}}$$

represents grams of PAO formed per grams of catalyst used in the oligomerization reaction.

High productivity rates are also achieved. In an embodiment, the productivity rate in the first oligomerization is greater than $$4,000 \frac{g_{PAO}}{g_{catalyst} * hour},$$

preferably greater than $$6,000 \frac{g_{PAO}}{g_{catalyst} * hour},$$

preferably greater than $$8,000 \frac{g_{PAO}}{g_{catalyst} * hour},$$

preferably greater than $$10,000 \frac{g_{PAO}}{g_{catalyst} * hour},$$

wherein $$\frac{g_{PAO}}{g_{catalyst}}$$

represents grams of PAO formed per grams of catalyst used in the oligomerization reaction.

Activator

The catalyst may be activated by a commonly known activator such as non-coordinating anion (NCA) activator. An NCA is an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the NCA. Suitable metals include, but are not limited to, aluminum, gold, and platinum. Suitable metalloids include, but are not limited to, boron, aluminum, phosphorus, and silicon.

Lewis acid and ionic activators may also be used. Useful but non-limiting examples of Lewis acid activators include triphenylboron, tris-perfluorophenylboron, tris-perfluorophenylaluminum, and the like. Useful but non-limiting examples of ionic activators include dimethylanilinium tetrakisperfluorophenylborate, triphenylcarbonium tetrakisperfluorophenylborate, dimethylanilinium tetrakisperfluorophenylaluminate, and the like.

An additional subclass of useful NCAs comprises stoichiometric activators, which can be either neutral or ionic. Examples of neutral stoichiometric activators include tri-substituted boron, tellurium, aluminum, gallium, indium, or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, alkenyl compounds, and mixtures thereof; preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. Ionic stoichiometric activator compounds may contain an active proton, or some other cation associated with, but not coordinated to, or only loosely coordinated to, the remaining ion of the ionizing compound.

Ionic catalysts can be prepared by reacting a transition metal compound with an activator, such as $B(C_6F_6)_3$, which upon reaction with the hydrolyzable ligand (X') of the transition metal compound forms an anion, such as ([B$(C_6F_5)_3(X')]^-$), which stabilizes the cationic transition metal species generated by the reaction. The catalysts can be, and preferably are, prepared with activator components which are ionic compounds or compositions. However, preparation of activators utilizing neutral compounds is also contemplated by this invention.

Compounds useful as an activator component in the preparation of the ionic catalyst systems used in the process of this invention comprise a cation, which is preferably a Brønsted acid capable of donating a proton, and a compatible NCA which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like.

In an embodiment, the ionic stoichiometric activators include a cation and an anion component, and may be represented by the following formula:

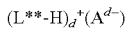

wherein:
L** is an neutral Lewis base;
H is hydrogen;
(L**-H)$_d^+$ is a Brønsted acid or a reducible Lewis Acid;
A$^{d-}$ is an NCA having the charge d;
and d is an integer from 1 to 3.

The cation component, (L**-H)$_d^+$ may include Brønsted acids such as protons or protonated Lewis bases or reducible Lewis acids capable of protonating or abstracting a moiety, such as an alkyl or aryl, from the catalyst after alkylation.

The activating cation (L-H)$_d^+$ may be a Brønsted acid, capable of donating a proton to the alkylated transition metal catalytic precursor resulting in a transition metal cation, including ammoniums, oxoniums, phosphoniums, silyliums, and mixtures thereof; preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L-H)$_d^+$ may also be a moiety such as silver, tropylium, carbeniums, ferroceniums, and mixtures thereof; preferably carboniums and ferroceniums; most preferably triphenyl carbonium. The anion component A$^{d-}$ include those having the formula [M$^{k+}$Q$_n$]$^{d-}$ wherein k is an integer from 1 to 3; n is an integer from 2-6; n–k=d; M is an element selected from Group 13 of the Periodic Table of the Elements, preferably boron or aluminum; and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ also include diboron compounds as disclosed in U.S. Pat. No. 5,447,895, which is incorporated herein by reference.

Illustrative but non-limiting examples of boron compounds which may be used as an NCA activator in combination with a co-activator are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, dialkyl ammonium salts such as: di-(iso-propyl)ammonium tetrakis(pentafluorophenyl)borate, and dicyclohexylammonium tetrakis(pentafluorophenyl)borate other salts such as: tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenylborate, triphenylcarbenium tetrakis(pentafluorophenylborate, triphenylphosphonium tetrakis(pentafluorophenyl)borate, triethylsilylium tetrakis(pentafluorophenyl)borate, benzene(diazonium)tetrakis (pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium)tetrakis(3,5-bis(trifluoromethyl)phenyl)borate.

In an embodiment, the NCA activator, (L**-H)$_d^+$(A$^{d-}$), is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl) borate, triphenylcarbenium tetrakis(3,5-bis(trifluoromethyl)phenyl)borate, or triphenylcarbenium tetra(perfluorophenyl)borate.

Pehlert et al., U.S. Pat. No. 7,511,104 provides additional details on NCA activators that may be useful in this invention, and these details are hereby fully incorporated by reference.

Additional activators that may be used include alumoxanes or alumoxanes in combination with an NCA. In one embodiment, alumoxane activators are utilized as an activator. Alumoxanes are generally oligomeric compounds containing —Al(R1)-O— sub-units, where R1 is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used.

A catalyst co-activator is a compound capable of alkylating the catalyst, such that when used in combination with an activator, an active catalyst is formed. Co-activators may include alumoxanes such as methylalumoxane, modified alumoxanes such as modified methylalumoxane, and aluminum alkyls such trimethylaluminum, tri-isobutylaluminum, triethylaluminum, tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the catalyst is not a dihydrocarbyl or dihydride complex.

The co-activator may also be used as a scavenger to deactivate impurities in feed or reactors. A scavenger is a compound that is sufficiently Lewis acidic to coordinate with polar contaminates and impurities adventitiously occurring in the polymerization feedstocks or reaction medium. Such impurities can be inadvertently introduced with any of the reaction components, and adversely affect catalyst activity and stability. Useful scavenging compounds may be organometallic compounds such as triethyl aluminum, triethyl borane, tri-isobutyl aluminum, methylalumoxane, isobutyl aluminumoxane, tri-n-hexyl aluminum, tri-n-octyl aluminum, and those having bulky substituents covalently bound to the metal or metalloid center being preferred to minimize adverse interaction with the active catalyst. Other useful scavenger compounds may include those mentioned in U.S. Pat. No. 5,241,025; EP-A 0426638; and WO 97/22635, which are hereby incorporated by reference for such details.

The reaction time or reactor residence time is usually dependent on the type of catalyst used, the amount of catalyst used, and the desired conversion level. Different transition metal compounds (also referred to as metallocene) have different activities. High amount of catalyst loading tends to give high conversion at short reaction time. However, high amount of catalyst usage make the production process uneconomical and difficult to manage the reaction heat or to control the reaction temperature. Therefore, it is useful to choose a catalyst with maximum catalyst productivity to minimize the amount of metallocene and the amount of activators needed. For the preferred catalyst system of metallocene plus a Lewis Acid or an ionic promoter with NCA component, the transition metal compound use is typically in the range of 0.01 microgram to 500 micrograms of metallocene component/gram of alpha-olefin feed. Usually the preferred range is from 0.1 microgram to 100 microgram of metallocene component per gram of alpha-olefin feed. Furthermore, the molar ratio of the NCA activator to metallocene is in the range from 0.1 to 10, preferably 0.5 to 5, preferably 0.5 to 3. For the co-activators of alkylaluminums, the molar ratio of the co-activator to metallocene is in the range from 1 to 1000, preferably 2 to 500, preferably 4 to 400.

In selecting oligomerization conditions, to obtain the desired first reactor effluent, the system uses the transition metal compound (also referred to as the catalyst), activator, and co-activator.

US 2007/0043248 and US 2010/029242 provides additional details of metallocene catalysts, activators, co-activators, and appropriate ratios of such compounds in the feedstock that may be useful in this invention, and these additional details are hereby incorporated by reference.

Oligomerization Process

Many oligomerization processes and reactor types used for single site- or metallocene-catalyzed oligomerizations such as solution, slurry, and bulk oligomerization processes may be used in this invention. In some embodiments, if a solid catalyst is used, a slurry or continuous fixed bed or plug flow process is suitable. In a preferred embodiment, the monomers are contacted with the metallocene compound and the activator in the solution phase, bulk phase, or slurry phase, preferably in a continuous stirred tank reactor or a continuous tubular reactor. In a preferred embodiment, the temperature in any reactor used herein is from −10° C. to 250° C., preferably from 30° C. to 220° C., preferably from 50° C. to 180° C., preferably from 80° C. to 150° C. In a preferred embodiment, the pressure in any reactor used herein is from 10.13 to 10132.5 kPa (0.1 to 100 atm/1.5 to 1500 psi), preferably from 50.66 to 7600 kPa (0.5 to 75 atm/8 to 1125 psi), and most preferably from 101.3 to 5066.25 kPa (1 to 50 atm/15 to 750 psi). In another embodiment, the pressure in any reactor used herein is from 101.3 to 5,066,250 kPa (1 to 50,000 atm), preferably 101.3 to 2,533,125 kPa (1 to 25,000 atm). In another embodiment, the residence time in any reactor is 1 second to 100 hours, preferably 30 seconds to 50 hours, preferably 2 minutes to 6 hours, preferably 1 to 6 hours. In another embodiment, solvent or diluent is present in the reactor. These solvents or diluents are usually pre-treated in same manners as the feed olefins.

The oligomerization can be run in batch mode, where all the components are added into a reactor and allowed to react to a degree of conversion, either partial or full conversion. Subsequently, the catalyst is deactivated by any possible means, such as exposure to air or water, or by addition of alcohols or solvents containing deactivating agents. The oligomerization can also be carried out in a semi-continuous operation, where feeds and catalyst system components are continuously and simultaneously added to the reactor so as to maintain a constant ratio of catalyst system components to feed olefin(s). When all feeds and catalyst components are added, the reaction is allowed to proceed to a pre-determined stage. The reaction is then discontinued by catalyst deactivation in the same manner as described for batch operation. The oligomerization can also be carried out in a continuous operation, where feeds and catalyst system components are continuously and simultaneously added to the reactor so as to maintain a constant ratio of catalyst system and feeds. The reaction product is continuously withdrawn from the reactor, as in a typical continuous stirred tank reactor (CSTR)

operation. The residence times of the reactants are controlled by a pre-determined degree of conversion. The withdrawn product is then typically quenched in the separate reactor in a similar manner as other operation. In a preferred embodiment, any of the processes to prepare PAOs described herein are continuous processes.

A production facility may have one single reactor or several reactors arranged in series or in parallel, or both, to maximize productivity, product properties, and general process efficiency. The catalyst, activator, and co-activator may be delivered as a solution or slurry in a solvent or in the LAO feed stream, either separately to the reactor, activated in-line just prior to the reactor, or pre-activated and pumped as an activated solution or slurry to the reactor. Oligomerizations are carried out in either single reactor operation, in which the monomer, or several monomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

The reactors and associated equipment are usually pretreated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds. Additionally, in one embodiment of any of the processes described herein, the feed olefins and/or solvents are treated to remove catalyst poisons, such as peroxides, oxygen or nitrogen-containing organic compounds or acetylenic compounds. Such treatment will increase catalyst productivity 2- to 10-fold or more.

The reaction time or reactor residence time is usually dependent on the type of catalyst used, the amount of catalyst used, and the desired conversion level. When the catalyst is a metallocene, different metallocenes have different activities. Usually, a higher degree of alkyl substitution on the cyclopentadienyl ring, or bridging improves catalyst productivity. High catalyst loading tends to give high conversion in short reaction time. However, high catalyst usage makes the process uneconomical and difficult to manage the reaction heat or to control the reaction temperature. Therefore, it is useful to choose a catalyst with maximum catalyst productivity to minimize the amount of metallocene and the amount of activators needed.

US 2007/0043248 and US 2010/0292424 provide significant additional details on acceptable oligomerization processes using metallocene catalysts, and the details of these processes, process conditions, catalysts, activators, co-activators, etc. are hereby incorporated by reference to the extent that they are not inconsistent with anything described in this disclosure.

Due to the low activity of some metallocene catalysts at high temperatures, low viscosity PAOs are typically oligomerized in the presence of added hydrogen at lower temperatures. The advantage is that hydrogen acts as a chain terminator, effectively decreasing molecular weight and viscosity of the PAO. Hydrogen can also hydrogenate the olefin, however, saturating the LAO feedstock and PAO. This would prevent LAO or the PAO dimer from being usefully recycled or used as feedstock into a further oligomerization process. Thus it is an improvement over prior art to be able to make an intermediate PAO without having to add hydrogen for chain termination because the unreacted LAO feedstock and intermediate PAO dimer maintain their unsaturation, and thus their reactivity, for a subsequent recycle step or use as a feedstock in a further oligomerization process.

The PAO produced is a mixture of dimers, trimers, and optionally tetramer and higher oligomers of the respective alpha olefin feedstocks. In an embodiment, the dimer portion of the intermediate PAO may be a reactor effluent that has not been subject to a distillation process. In another embodiment, the dimer portion of the PAO may be subjected to a distillation process to separate it from unreacted monomers, and the trimer and optional higher oligomer portion prior to feeding the at least dimer portion to a second reactor for further oligomerization. In a further embodiment, the trimer portion of the PAO and the tetramer and higher oligomer portion of the PAO can be isolated by distillation. In another embodiment, the PAO is not subjected to a separate isomerization process following oligomerization.

In the invention, the PAO product has a kinematic viscosity at 100° C. ($KV_{100}$) of less than 20 cSt, preferably less than 15 cSt, preferably less than 12 cSt, more preferably less than 10 cSt. In the invention, the PAO trimer portion after a hydrogenation step has a $KV_{100}$ of less than 4 cSt, preferably less than 3.6 cSt. In an embodiment, the tetramers and higher oligomer portion of the intermediate PAO after a hydrogenation step has a $KV_{100}$ of less than 30 cSt. In an embodiment, the PAO oligomer portion remaining after the PAO dimer portion is removed has a $KV_{100}$ of less than 25 cSt.

The intermediate PAO trimer portion has a VI of greater than 125, preferably greater than 130. In an embodiment, the trimer and higher oligomer portion of the intermediate PAO has a VI of greater than 130, preferably greater than 135. In an embodiment, the tetramer and higher oligomer portion of the intermediate PAO has a VI of greater than 150, preferably greater than 155.

The intermediate PAO trimer portion has a Noack volatility that is less than 15 wt %, preferably less than 14 wt %, preferably less than 13 wt %, preferably less than 12 wt %. In an embodiment, the intermediate PAO tetramers and higher oligomer portion has a Noack volatility that is less than 8 wt %, preferably less than 7 wt %, preferably less than 6 wt %.

In an embodiment, the intermediate PAO dimer portion has a number average molecular weight in the range of 120 to 600.

The intermediate PAO dimer portion possesses at least one carbon-carbon unsaturated double bond. In an embodiment, a portion of this intermediate PAO dimer comprises tri-substituted vinylene. This tri-substituted vinylene has two possible isomer structures that may coexist and differ regarding where the unsaturated double bond is located, as represented by the following structure:

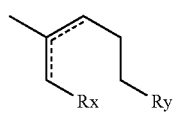

wherein the dashed line represents the two possible locations where the unsaturated double bond may be located and Rx and Ry are independently selected from a $C_3$ to $C_{21}$ alkyl group, preferably from linear $C_3$ to $C_{21}$ alkyl group.

In an embodiment, the intermediate PAO dimer contains greater than 20 wt %, preferably greater than 25 wt %, preferably greater than 30 wt %, preferably greater than 40 wt %, preferably greater than 50 wt %, preferably greater than 60 wt %, preferably greater than 70 wt %, preferably greater than 80 wt % of tri-substituted vinylene olefins represented by the general structure above.

In a preferred embodiment, Rx and Ry are independently $C_3$ to $C_{11}$ alkyl groups. In a preferred embodiment, Rx and Ry are both $C_2$. In a preferred embodiment, the intermediate PAO dimer comprises a portion of tri-substituted vinylene dimer that is represented by the following structure:

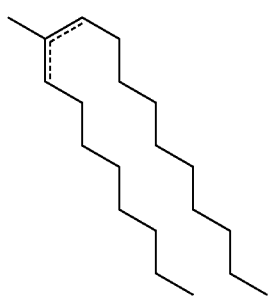

wherein the dashed line represents the two possible locations where the unsaturated double bond may be located.

In any embodiment, the intermediate PAO contains less than 70 wt %, preferably less than 60 wt %, preferably less than 50 wt %, preferably less than 40 wt %, preferably less than 30 wt %, preferably less than 20 wt % of di-substituted vinylidene represented by the formula:

$$RqRzC=CH_2$$

wherein Rq and Rz are independently selected from alkyl groups, preferably linear alkyl groups, or preferably $C_3$ to $C_{21}$ linear alkyl groups.

One embodiment of the first oligomerization is illustrated and explained below as a non-limiting example. First, the following reactions show alkylation of a metallocene catalyst with tri n-octyl aluminum followed by activation of the catalyst with N,N-Dimethylanilinium tetrakis(penta-fluorophenyl)borate (1-):

Catalyst Alkylation

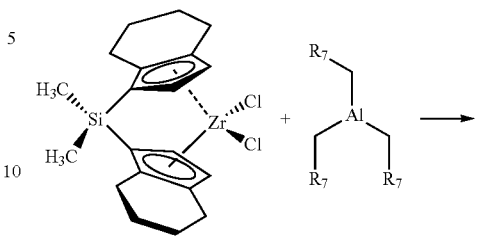

Catalyst Activation

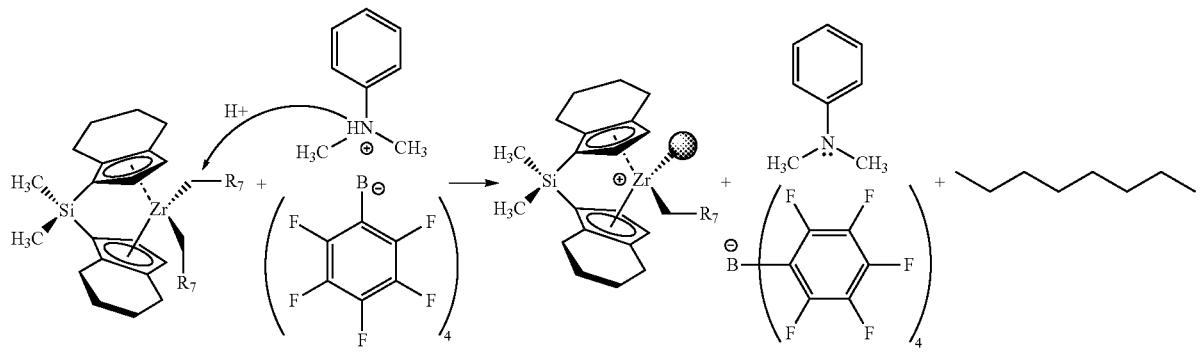

Following catalyst activation, a 1,2 insertion process may take place as shown below:

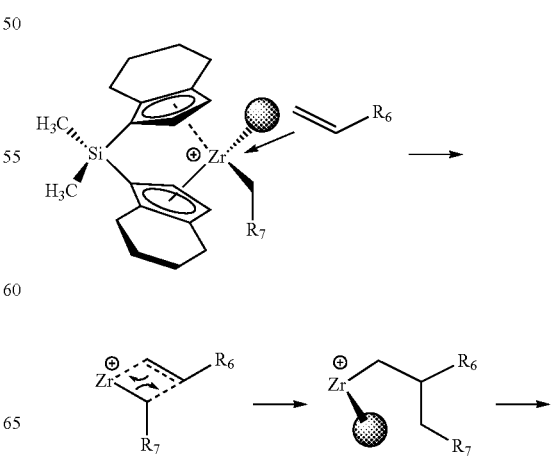

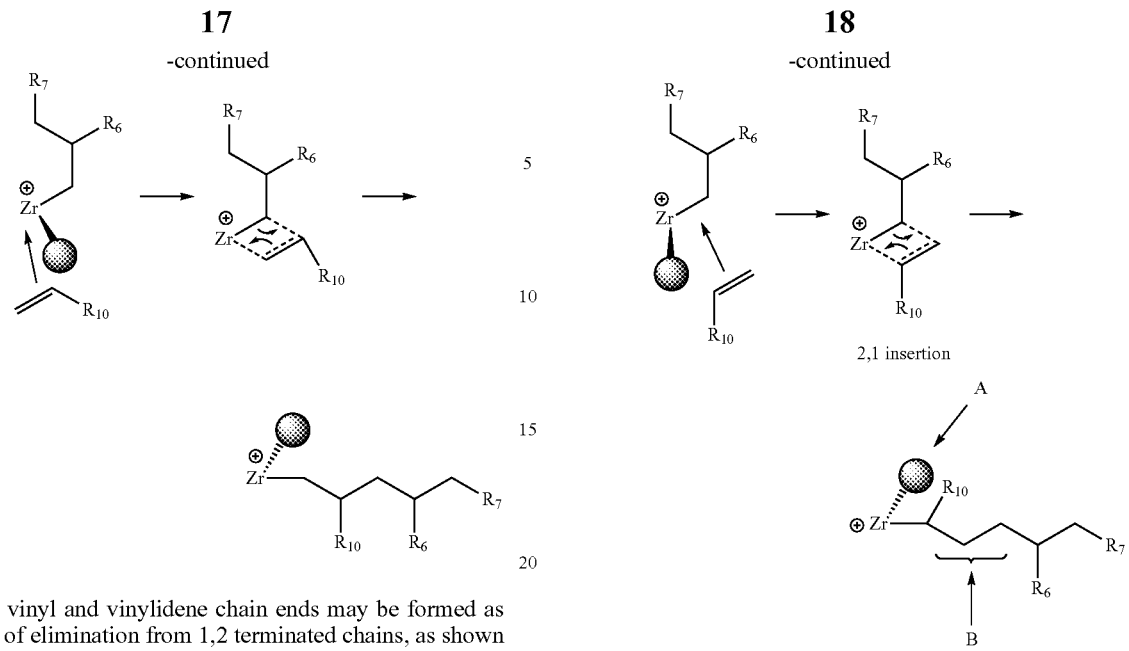

Both vinyl and vinylidene chain ends may be formed as a result of elimination from 1,2 terminated chains, as shown below. This chain termination mechanism shown below competes with propagation during this reaction phase.

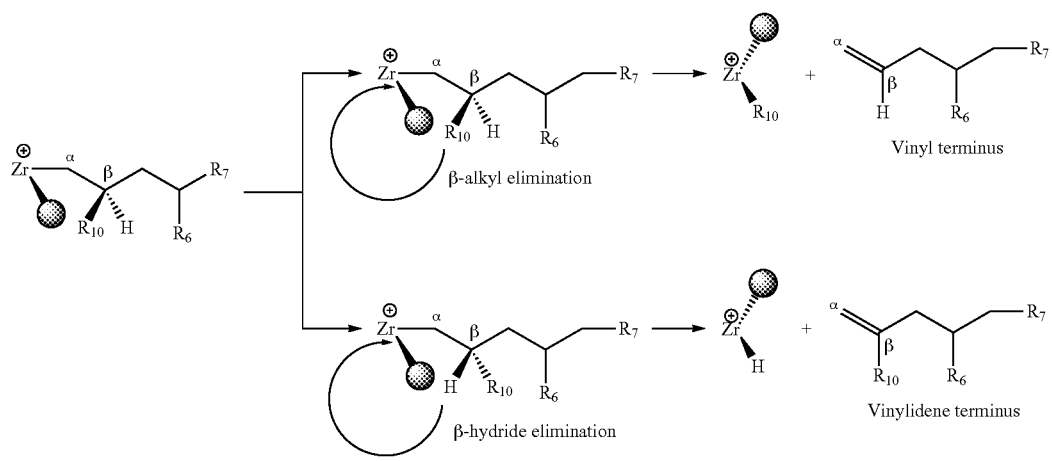

Alternatively following catalyst activation, a 2,1 insertion process may take place as shown below:

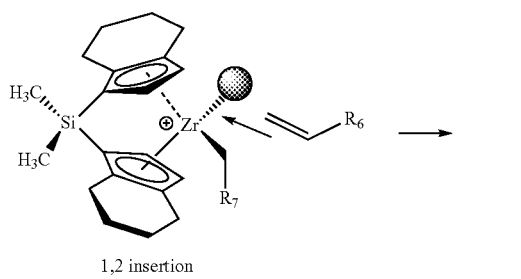

Elimination is favored over propagation after 2,1 insertions due to the proximity of the alpha alkyl branch to the active center (see the area identified with the letter "A" in the reaction above). In other words, the more crowded active site hinders propagation and enhances elimination. 2,1 insertions are easily detected by nuclear magnetic resonance (NMR) using signals from the unique methylene-methylene unit (see the area identified with the letter "B" in the reaction above).

Certain metallocene catalysts result in a higher occurrence of 2,1 insertions, and elimination from 2,1 terminated chains preferentially forms vinylene chain ends, as shown below.

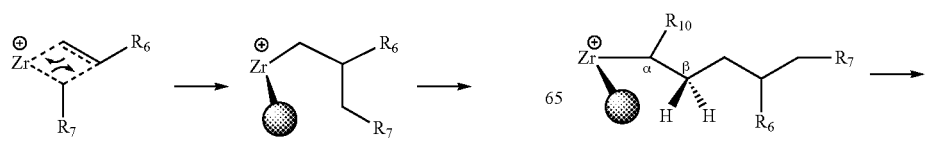

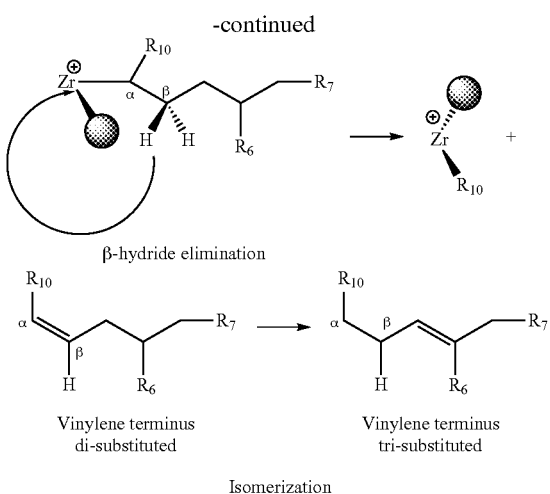

β-hydride elimination

Vinylene terminus
di-substituted

Vinylene terminus
tri-substituted

Isomerization

Subsequent Oligomerization

Products from the oligomerization discussed above, also referenced as 'the first oligomerization', may be used in subsequent oligomerizations. The PAO dimer may be used as the sole olefin feedstock to the subsequent oligomerization or it may be used together with an alpha olefin feedstock of the type used as the olefin starting material for the first oligomerization. Other portions of the effluent from the oligomerization may also be used as a feedstock to a subsequent oligomerization, including unreacted LAO. The PAO dimer may suitably be separated from the overall PAO product by distillation, with the cut point set at a value dependent upon the fraction to be used as lube base stock or the fraction to be used as feed for the subsequent oligomerization. Alpha olefins with the same attributes as those preferred for the first oligomerization are preferred for the subsequent oligomerization. Any oligomerization process and catalyst may be used for a subsequent oligomerization. A preferred catalyst for the subsequent oligomerization is a non-transition metal catalyst, and preferably a Lewis acid catalyst. Patent applications US 2009/0156874 and US 2009/0240012 describe a preferred process for the subsequent oligomerization, to which reference is made for details of feedstocks, compositions, catalysts and co-catalysts, and process conditions. The Lewis acid catalysts of US 2009/0156874 and US 2009/0240012 include the metal and metalloid halides conventionally used as Friedel-Crafts catalysts, examples include $AlCl_3$, $BF_3$, $AlBr_3$, $TiCl_3$, and $TiCl_4$ either alone or with a protic promoter. Boron trifluoride is commonly used but not particularly suitable unless it is used with a protic promoter. Useful co-catalysts are well known and described in detail in US 2009/0156874 and US 2009/0240012. Solid Lewis acid catalysts, such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates (e.g., $WOx/ZrO_2$, $WOx/MoO_3$) may also be used although these are not generally as favored economically. Additional process conditions and other details are described in detail in US 2009/0156874 and US 2009/0240012, and incorporated herein by reference.

The structure of the invented intermediate PAO is such that, when reacted in a subsequent oligomerization, the intermediate PAO reacts preferentially with the optional LAO to form a co-dimer of the dimer and LAO at high yields. This allows for high conversion and yield rates of the desired PAO products. In an embodiment, the PAO product from the subsequent oligomerization comprises primarily a co-dimer of the dimer and the respective LAO feedstock. In an embodiment, where the LAO feedstock for both oligomerization steps is 1-decene, the incorporation of intermediate $C_{20}$ PAO dimer into higher oligomers is greater than 80%, the conversion of the LAO is greater than 95%, and the yield % of $C_{30}$ product in the overall product mix is greater than 75%. In another embodiment, where the LAO feedstock is 1-octene, the incorporation of the intermediate PAO dimer into higher oligomers is greater than 85%, the conversion of the LAO is greater than 90%, and the yield % of $C_{28}$ product in the overall product mix is greater than 70%. In another embodiment, where the feedstock is 1-dodecene, the incorporation of the intermediate PAO dimer into higher oligomers is greater than 90%, the conversion of the LAO is greater than 75%, and the yield % of $C_{32}$ product in the overall product mix is greater than 70%.

The PAOs produced in the subsequent oligomerization may be a mixture of dimers, trimers, and optionally tetramer and higher oligomers. This PAO is referred to interchangeably as the "second reactor effluent" from which unreacted monomer may be optionally removed and recycled back to the second reactor. The desirable properties of the intermediate PAO dimer enable a high yield of a co-dimer of intermediate PAO dimer and LAO in the second reactor effluent. The PAOs in the second reactor effluent are especially notable because very low viscosity PAOs are achieved at very high yields and these PAOs have excellent rheological properties, including low pour point, outstanding Noack volatility, and very high viscosity indexes.

In an embodiment, this PAO may contain trace amounts of transition metal compound if the catalyst in the intermediate or subsequent oligomerization is a metallocene catalyst. A trace amount of transition metal compound is defined for purposes of this disclosure as any amount of transition metal compound or Group 4 metal present in the PAO. Presence of Group 4 metal may be detected at the ppm or ppb level by ASTM 5185 or other methods known in the art.

The second reactor effluent PAO has a portion having a carbon count of $C_{28}$-$C_{32}$, wherein the $C_{28}$-$C_{32}$ portion is at least 65 wt %, preferably at least 70 wt %, preferably at least 75 wt %, more preferably at least 80 wt % of the second reactor effluent.

The kinematic viscosity at 100° C. of the second reactor PAO is less than 10 cSt, preferably less than 6 cSt, preferably less than 4.5 cSt, preferably less than 3.2 cSt, or preferably in the range of 2.8 to 4.5 cSt. The kinematic viscosity at 100° C. of the $C_{28}$ portion of the PAO is less than 3.2 cSt. In an embodiment, the kinematic viscosity at 100° C. of the $C_{28}$ to $C_{32}$ portion of the PAO is less than 10 cSt, preferably less than 6 cSt, preferably less than 4.5 cSt, and preferably in the range of 2.8 to 4.5 cSt.

The pour point of the second reactor PAO is below −40° C., preferably below −50° C., preferably below −60° C., preferably below −70° C., or preferably below −80° C. The pour point of the $C_{28}$ to $C_{32}$ portion of the PAO is below −30° C., preferably below −40° C., preferably below −50° C., preferably below −60° C., preferably below −70° C., or preferably below −80° C.

The Noack volatility of the second reactor PAO is not more than 9.0 wt %, preferably not more than 8.5 wt %, preferably not more than 8.0 wt %, or preferably not more than 7.5 wt %. The Noack volatility of the $C_{28}$ to $C_{32}$ portion of the PAO is less than 19 wt %, preferably less than 14 wt %, preferably less than 12 wt %, preferably less than 10 wt %, or more preferably less than 9 wt %.

The viscosity index of the second reactor PAO is more than 121, preferably more than 125, preferably more than 130, or preferably more than 136. The viscosity index of the trimer or $C_{28}$ to $C_{32}$ portion of the second reactor PAO is above 120, preferably above 125, preferably above 130, or more preferably at least 135.

The cold crank simulator value (CCS) at −25° C. of the second reactor PAO or a portion of the second reactor PAO is not more than 500 cP, preferably not more than 450 cP, preferably not more than 350 cP, preferably not more than 250 cP, preferably in the range of 200 to 450 cP, or preferably in the range of 100 to 250 cP.

In an embodiment, the second reactor PAO has a kinematic viscosity at 100° C. of not more than 3.2 cSt and a Noack volatility of not more than 19 wt %. In another embodiment, the second reactor PAO has a kinematic viscosity at 100° C. of not more than 4.1 cSt and a Noack volatility of not more than 9 wt %.

The ability to achieve such low viscosity PAOs with such low Noack volatility at such high yields is especially remarkable, and highly attributable to the intermediate PAO tri-substituted vinylene dimer having properties that make it especially desirable in the subsequent oligomerization process.

The mPAOs and PAOs produced in any subsequent oligomerization processes, particularly those of ultra-low viscosity, are especially suitable for high performance automotive engine oil formulations either by themselves or by blending with other fluids, such as Group II, Group II+, Group III, Group III+ or lube basestocks derived from hydroisomerization of wax fractions from Fisher-Tropsch hydrocarbon synthesis from $CO/H_2$ syn gas, or other Group IV or Group V basestocks. They are also preferred grades for high performance industrial oil formulations that call for ultra-low and low viscosity oils. Additionally, they are also suitable for use in personal care applications, such as soaps, detergents, creams, lotions, shampoos, detergents, etc.

EXAMPLES

The various test methods and parameters used to describe the intermediate PAO and the final PAO are summarized in Table 2 below and some test methods are described in the below text.

Nuclear magnetic resonance spectroscopy (NMR), augmented by the identification and integration of end group resonances and removal of their contributions to the peak areas, were used to identify the structures of the synthesized oligomers and quantify the composition of each structure.

Proton NMR (also frequently referred to as HNMR) spectroscopic analysis can differentiate and quantify the types of olefinic unsaturation: vinylidene, 1,2-disubstituted, trisubstituted, or vinyl. Carbon-13 NMR (referred to simply as C-NMR) spectroscopy can confirm the olefin distribution calculated from the proton spectrum. Both methods of NMR analysis are well known in the art.

For any HNMR analysis of the samples a Varian pulsed Fourier transform NMR spectrometer equipped with a variable temperature proton detection probe operating at room temperature was utilized. Prior to collecting spectral data for a sample, the sample was prepared by diluting it in deuterated chloroform ($CDCl_3$) (less than 10% sample in chloroform) and then transferring the solution into a 5 mm glass NMR tube. Typical acquisition parameters were SW>10 ppm, pulse width <30 degrees, acquisition time=2 s, acquisition delay=5 s and number of co-added spectra=120. Chemical shifts were determined relative to the $CDCl_3$ signal set to 7.25 ppm.

Quantitative analysis of the olefinic distribution for structures in a pure dimer sample that contain unsaturated hydrogen atoms was performed by HNMR and is described below. Since the technique detects hydrogen, any unsaturated species (tetrasubstituted olefins) that do not contain olefinic hydrogens are not included in the analysis (C-NMR must be used for determining tetrasubstituted olefins). Analysis of the olefinic region was performed by measuring the normalized integrated intensities in the spectral regions shown in Table 1. The relative number of olefinic structures in the sample were then calculated by dividing the respective region intensities by the number of olefinic hydrogen species in the unsaturated structures represented in that region. Finally, percentages of the different olefin types were determined by dividing the relative amount of each olefin type by the sum of these olefins in the sample.

TABLE 1

| Region Chemical Shift (ppm) | Olefinic Species type | Number of Hydrogens in Olefinic Species |
|---|---|---|
| 4.54 to 4.70 | Vinylidene | 2 |
| 4.74 to 4.80 and 5.01 to 5.19 | Trisubstituted | 1 |
| 5.19 to 5.60 | Disubstituted Vinylene | 2 |

C-NMR was used to identify and quantify olefinic structures in the fluids. Classification of unsaturated carbon types that is based upon the number of attached hydrogen atoms was determined by comparing spectra collected using the APT (Patt, S. L.; Shoolery, N., J. Mag. Reson., 46:535 (1982)) and DEPT (Doddrell, D. M.; Pegg, D. T.; Bendall, M. R., J. Mag. Reson., 48:323 (1982)) pulse sequences. APT data detects all carbons in the sample and DEPT data contains signals from only carbons that have attached hydrogens. Carbons having odd number of hydrogen atoms directly attached are represented with signals with having an opposite polarity from those having two (DEPT data) or in the case of the APT spectra zero or two attached hydrogens. Therefore, the presence of a carbon signal in an APT spectra that is absent in the DEPT data and which has the same signal polarity as a carbon with two attached hydrogen atoms is indicative of a carbon without any attached hydrogens. Carbon signals exhibiting this polarity relationship that are in the chemical shift range between 105 and 155 ppm in the spectrum are classified as carbons in olefinic structures.

With olefinic carbons previously being classified according to the number of hydrogens that are attached, signal intensity can be used to identify the two carbons that are bonded together in an unsaturated structure. The intensities used were evaluated from a C-NMR spectrum that was collected using quantitative conditions. Because each olefinic bond is composed of a pair of carbons the signal intensity from each will be similar. Thus, by matching intensities to the carbon types identified above, different kinds of olefinic structures present in the sample were determined. As already discussed previously, vinyl olefins are defined as containing one unsaturated carbon that is bonded to two hydrogens bonded to a carbon that contains one hydrogen, vinylidene olefins are identified as having a carbon with two hydrogens bonded to a carbon without any attached hydrogens, and trisubstituted olefins are identified by having both carbons in the unsaturated structure contain one hydrogen atom. Tetrasubstituted olefin carbons are unsaturated structures in which neither of the carbons in the unsaturated structure have any directly bonded hydrogens.

A quantitative C-NMR spectrum was collected using the following conditions: 50 to 75 wt % solutions of the sample in deuterated chloroform containing 0.1 M of the relaxation agent $Cr(acac)_3$ (tris(acetylacetonato)-chromium (III)) was placed into a NMR spectrometer. Data was collected using a 30 degree pulse with inverse gated $^1H$ decoupling to suppress any nuclear Overhauser effect and an observe sweep width of 200 ppm.

Quantitation of the olefinic content in the sample is calculated by ratioing the normalized average intensity of the carbons in an olefinic bond multiplied by 1000 to the total carbon intensity attributable to the fluid sample. Percentages of each olefinic structure can be calculated by summing all of the olefinic structures identified and dividing that total into the individual structure amounts.

Gas chromatography (GC) was used to determine the composition of the synthesized oligomers by molecular weight. The gas chromatograph is a HP model equipped with a 15 meter dimethyl siloxane. A 1 microliter sample was injected into the column at 40° C., held for 2 minutes, program-heated at 11° C. per minute to 350° C. and held for 5 minutes. The sample was then heated at a rate of 20° C. per minute to 390° C. and held for 17.8 minutes. The content of the dimer, trimer, tetramer of total carbon numbers less than 50 can be analyzed quantitatively using the GC method. The distribution of the composition from dimer, trimer and tetramer and/or pentamer can be fit to a Bernoullian distribution and the randomness can be calculated from the difference between the GC analysis and best fit calculation.

TABLE 2

| Parameter | Units | Test |
| --- | --- | --- |
| Viscosity Index (VI) | — | ASTM Method D-2270 |
| Kinematic Viscosity (KV) | cSt | ASTM Method D-445, measured at either 100° C. or 40° C. |
| Noack Volatility | % | ASTM D 5800 |
| Pour Point | ° C. | ASTM D-97 |
| Molecular Weights, Mn, Mw | | GC, See above text |
| Cold Crank Simulator (CCS) | | ASTM D-5293 |
| Oligomer structure identification | | Proton NMR, See above text |
| Oligomer structure quantification | % | $C^{13}$ NMR, See above text |

Example 1

A 97% pure 1-decene was fed to a stainless steel Parr reactor where it was sparged with nitrogen for 1 hour to obtain a purified feed. The purified stream of 1-decene was then fed at a rate of 2080 grams per hour to a stainless steel Parr reactor for oligomerization. The oligomerization temperature was 120° C. The catalyst was dimethylsilyl-bis(tetrahydroindenyl)zirconium dimethyl (hereinafter referred to as "Catalyst 1"). A catalyst solution including purified toluene, tri n-octyl aluminum (TNOA), and N,N-dimethyl-anilinium tetrakis(penta-fluorophenyl)borate (hereinafter referred to as "Activator 1") was prepared per the following recipe based on 1 gram of Catalyst 1:

| Catalyst 1 | 1 gram |
| --- | --- |
| Purified Toluene | 376 grams |
| 25% TNOA in Toluene | 24 grams |
| Activator 1 | 1.9 grams |

The 1-decene and catalyst solution were fed into the reactor at a ratio of 31,200 grams of LAO per gram of catalyst solution. Additional TNOA was also used as a scavenger to remove any polar impurities and added to the reactor at a rate of 0.8 grams of 0.25% TNOA in toluene per 100 grams of purified LAO. The residence time in the reactor was 2.7 hours. The reactor was run at liquid full conditions, with no addition of any gas. When the system reached steady-state, a sample was taken from the reactor effluent and the dimer portion was separated by distillation. The mass percentage of each type of olefin in the distilled intermediate PAO dimer, as determined by proton NMR, is shown in Table 3. This example provides a characterization of the olefinic composition of the intermediate PAO dimer formed in the first step of the process of the invention.

TABLE 3

| Olefin Type | Percent by Mass of Olefin in Dimer Mixture |
| --- | --- |
| Vinylidene | 29% |
| Tri-substituted Vinylene | 60% |
| di-substituted vinylene | 11% |

Example 2

The reactor effluent from Example 1 was distilled to remove the unreacted LAO and to separate the olefin fractions. The different olefin fractions were each hydrogenated in a stainless steel Parr reactor at 232° C. and 2413 kPa (350 psi) of hydrogen for 2 hours using 0.5 wt % Nickel Oxide catalyst. Properties of each hydrogenated distillation cut are shown in Table 4. This example demonstrates that, with the exception of the intermediate PAO dimer, the intermediate PAO cuts have excellent properties.

TABLE 4

| Component | Oligomer Yield (%)* | KV at 100° C. (cSt) | KV at 40° C. (cSt) | VI | Pour Point (° C.) | Noack Volatility (%) |
| --- | --- | --- | --- | --- | --- | --- |
| Intermediate PAO Dimer (C20) | 33 | 1.79 | 4.98 | N/A | −12 | N/A |
| Intermediate PAO Trimer (C30) | 31 | 3.39 | 13.5 | 128 | −75 | 12.53 |
| Intermediate PAO Tetramer+ (C40+) | 31 | 9.34 | 53.57 | 158 | −66 | 3.15 |

*Yields reported are equivalent to mass % of reactor effluent; 6% of reactor effluent was monomer.

Example 3 mPAO dimer portion from a reaction using the procedure of Example 1 (and therefor having the properties/components listed above), and prior to any hydrogenation of the dimer, was oligomerized with 1-decene in a stainless steel Parr reactor using a $BF_3$ catalyst promoted with a $BF_3$ complex of butanol and butyl acetate. The intermediate PAO dimer was fed at a mass ratio of 2:1 to the 1-decene. The reactor temperature was 32° C. with a 34.47 kPa (5 psi) partial pressure of $BF_3$ and catalyst concentration was 30 mmol of catalyst per 100 grams of feed. The catalyst and feeds were stopped after one hour and the reactor contents were allowed to react for one hour. A sample was then collected and analyzed by GC. Table 5 compares conversion of the intermediate PAO dimer and conversion of the 1-decene. Table 6 gives properties and yield of the PAO co-dimer resulting from the reaction of the LAO and intermediate PAO dimer The data in Tables 5 and 6 demonstrate that the intermediate PAO dimer from Example 1 is highly reactive in an acid catalyzed oligomerization and that it produces a co-dimer with excellent properties. Because the 1-decene dimer has the same carbon number as the intermediate mPAO dimer, it is difficult to determine exactly how much intermediate mPAO dimer was converted. Table 4 specifies the least amount of intermediate PAO dimer converted (the assumption being that all dimer in the reactor effluent was unreacted intermediate PAO) and also the estimated amount converted, calculated by assuming that only the linear portion of the dimer GC peak is unreacted intermediate PAO dimer and the other portion is formed by the dimerization of the 1-decene.

Example 4

The procedure of Example 3 was followed, except that the unhydrogenated intermediate PAO dimer portion was reacted with 1-octene instead of 1-decene. Results are shown in Tables 5 and 6 below. Because the 1-octene dimer has a different carbon number than the intermediate PAO dimer, conversion of the intermediate PAO dimer is measured and need not be estimated.

Example 5

The procedure of Example 3 was followed, except that the unhydrogenated intermediate PAO dimer portion was reacted with 1-dodecene instead of 1-decene. Results are shown in Tables 5 and 6 below.

TABLE 5

| Example | LAO Feed | Conversion of Intermediate mPAO Dimer | Conversion of LAO | Conversion Intermediate mPAO Dimer/Conversion LAO |
|---|---|---|---|---|
| 3 | 1-decene | >80% (95% estimated) | 97% | >.82 (.98 estimated) |
| 4 | 1-octene | 89% | 91% | .98 |
| 5 | 1-dodecene | 91% | 79% | 1.15 |

Example 6

A trimer was oligomerized from 1-decene in a stainless steel Parr reactor using a $BF_3$ catalyst promoted with a $BF_3$ complex of butanol and butyl acetate. The reactor temperature was 32° C. with a 34.47 kPa (5 psi) partial pressure of $BF_3$ and catalyst concentration was 30 mmol of catalyst per 100 grams of feed. The catalyst and feeds were stopped after one hour and the reactor contents were allowed to react for one hour. These are the same conditions that were used in the reactions of Examples 3 to 5, except that 1-decene was fed to the reactor without any intermediate PAO dimer. A sample of the reaction effluent was then collected and analyzed by GC. Table 6 shows properties and yield of the resulting PAO trimer. This example is useful to show a comparison between an acid based oligomerization process with a pure LAO feed (Example 6) versus the same process with a mixed feed of the inventive intermediate mPAO dimer from Example 1 and LAO (Examples 3-5). The addition of the intermediate mPAO dimer contributes to a higher trimer yield and this trimer has improved VI and Noack Volatility.

TABLE 6

| Example | Co-dimer Yield (%) | KV at 100° C. (cSt) | KV at 40° C. (cSt) | VI | Pour Point (° C.) | Noack Volatility (%) |
|---|---|---|---|---|---|---|
| 3 | 77 | 3.52 | 13.7 | 129 | −75 | 9.97 |
| 4 | 71 | 3.20 | 12.5 | 124 | −81 | 18.1 |
| 5 | 71 | 4.00 | 16.9 | 139 | −66 | 7.23 |
| 6 | 62 | 3.60 | 15.3 | 119 | −75 | 17.15 |

Example 7

The intermediate mPAO dimer portion from a reaction using the procedure and catalysts system of Example 1 was oligomerized with 1-octene and 1-dodecene using an $AlCl_3$ catalyst in a five liter glass reactor. The intermediate mPAO dimer portion comprised 5% by mass of the combined LAO and dimer feed stream. The reactor temperature was 36° C., pressure was atmospheric, and catalyst concentration was 2.92% of the entire feed. The catalyst and feeds were stopped after three hours and the reactor contents were allowed to react for one hour. A sample was then collected and analyzed. Table 7 shows the amount of dimer in the reactor effluent as measured by GC (i.e. new dimer formed, and residual intermediate dimer) and the effluent's molecular weight distribution as determined by GPC.

Example 8

1-octene and 1-dodecene were fed to a reactor without any intermediate mPAO dimer following the same conditions and catalysts used in Example 7. Table 7 shows the amount of dimer in the reactor effluent and the effluent's molecular weight distribution. Comparing Examples 7 and 8 shows the addition of the intermediate mPAO dimer with high tri-substituted vinylene content to an acid catalyst process yielded a product with a similar weight distribution but with less dimer present; the lower dimer amounts being a commercially preferable result due to limited use of the dimer as a lubricant basestock.

TABLE 7

| Example | Dimer (mass %) | Mw/Mn | Mz/Mn |
|---|---|---|---|
| 7 | 0.79 | 1.36 | 1.77 |
| 8 | 1.08 | 1.36 | 1.76 |

Example 9

A 97% pure 1-decene was fed to a stainless steel Parr reactor where it was sparged with nitrogen for 1 hour to obtain a purified feed. The purified stream of 1-decene was then fed at a rate of 2080 grams per hour to a stainless steel Parr reactor for oligomerization. The oligomerization temperature was 120° C. The catalyst was Catalyst 1 prepared in a catalyst solution including purified toluene, tri n-octyl aluminum (TNOA), and Activator 1. The recipe of the catalyst solution, based on 1 gram of Catalyst 1, is provided below:

| Catalyst 1 | 1 gram |
|---|---|
| Purified Toluene | 376 grams |
| 25% TNOA in Toluene | 24 grams |
| Activator 1 | 1.9 grams |

The 1-decene and catalyst solution were fed into the reactor at a ratio of 31,200 grams of LAO per gram of catalyst solution. Additional TNOA was also used as a scavenger to remove any polar impurities and added to the LAO at a rate of 0.8 grams of 0.25% TNOA in toluene per 100 grams of purified LAO. The residence time in the reactor was 2.8 hours. The reactor was run at liquid full conditions, with no addition of any gas. When the system reached steady-state, a sample was taken from the reactor effluent and the composition of the crude polymer was determined by GC. The percent conversion of LAO, shown in Table 8, was computed from the GC results. Kinematic viscosity of the intermediate PAO product (after monomer removal) was measured at 100° C.

Example 10

The procedure of Example 9 was followed with the exception that the reactor temperature was 110° C.

Example 11

The procedure of Example 9 was followed with the exception that the reactor temperature was 130° C.

Example 12

The procedure of Example 9 was followed with the exception that the residence time in the reactor was 2 hours and the catalyst amount was increased to 23,000 grams of LAO per gram of catalyst to attain a similar conversion as the above Examples.

Example 13

The procedure of Example 9 was followed with the exception that the residence time in the reactor was 4 hours and the catalyst amount was decreased to 46,000 grams of LAO per gram of catalyst to attain a similar conversion as the above Examples.

Example 14

The procedure of Example 9 was followed with the exception that the reactor was run in semi-batch mode (the feed streams were continuously added until the desired amount was achieved and then the reaction was allowed to continue without addition new feedstream) and the catalyst used was bis(1-butyl-3-methyl cyclopentadienyl)zirconium dichloride (hereinafter referred to as "Catalyst 2") that had been alkylated with an octyl group by TNOA. In this Example, conversion of LAO was only 44%. The kinematic viscosity at 100° C. is not reported due to low conversion.

TABLE 8

| Example | Catalyst System/Catalyst Concentration (g LAO/g Cat) | Reaction Temp (° C.) | Residence Time in Reactor (hrs) | Conversion of LAO (% mass) | Effluent Kinematic Viscosity at 100° C. (cSt) | Intermediate PAO Kinematic Viscosity at 100° C. (cSt) |
|---|---|---|---|---|---|---|
| 9 | Catalyst 1/31,200 | 120 | 2.8 | 94 | 2.45 | 2.73 |
| 10 | Catalyst 1/31,200 | 110 | 2.8 | 93 | 3.26 | 3.55 |
| 11 | Catalyst 1/31,200 | 130 | 2.8 | 91 | 2.11 | 2.36 |
| 12 | Catalyst 1/23,000 | 120 | 2 | 94 | 2.42 | 2.77 |
| 13 | Catalyst 1/46,000 | 120 | 4 | 93 | 2.50 | 2.84 |
| 14 | Catalyst 2 (octylated)/31,200 | 120 | 2.8 | 44 | — | — |

Example 15

A dimer was formed using a process similar to what is described in U.S. Pat. No. 4,973,788. The LAO feedstock was 1-decene and TNOA was used as a catalyst. The contents were reacted for 86 hours at 120° C. and 172.37 kPa (25 psi) in a stainless steel Parr reactor. Following this, the dimer product portion was separated from the reactor effluent via distillation and its composition was analyzed via proton-NMR and is provided in Table 9.

TABLE 9

| Vinylidene | 96% |
|---|---|
| Di-substituted olefins | 4% |
| Tri-substituted olefins | 0% |

This $C_{20}$ dimer portion was then contacted with a 1-octene feedstock and a butanol/butyl acetate promoter system in a second stainless steel Parr reactor. The molar feed ratio of dimer to LAO was 1:1, the molar feed ratio of butanol to butyl acetate was 1:1, and the promoter was fed at a rate of 30 mmol/100 grams of LAO. The reaction temperature was 32° C. with a 34.47 kPa (5 psi) partial pressure of $BF_3$ providing the acid catalyst, the feed time was one hour, and then the contents were allowed to react for another hour. A sample was then taken from the product stream and analyzed via GC. The composition is provided below in Table 10. Applicants believe the dimer composition and other feedstocks used in this Example 15 are similar to the dimer composition and feedstocks used in multiple examples in U.S. Pat. No. 6,548,724.

Example 16

This example was based on an intermediate mPAO dimer resulting from a reaction using the procedure and catalyst system of Example 1; the resulting intermediate mPAO dimer had the same composition as set forth in Table 3. The intermediate mPAO dimer portion was reacted in a second reactor under feedstock and process conditions identical to the second oligomerization of Example 15. A sample of the PAO produced from the second oligomerization was taken from the product stream and analyzed via GC for its composition and the analysis is provided below in Table 10 (it is noted that this Example is a repeat of Example 4; the analyzed data is substantially similar for this second run of the same reactions and resulting PAO obtained from oligomerizing a primarily tri-substituted olefin).

TABLE 10

| Second reactor effluent | Example 15 | Example 16 |
|---|---|---|
| Unreacted monomer | 0.3% | 0.7% |
| Lighter fractions | 22.0% | 13.2% |
| $C_{28}$ fraction | 59.0% | 72.5% |
| Heavier fractions | 18.7% | 13.6% |

The yield of the $C_{28}$ fraction was increased from 59.0% to 72.5% by utilizing an intermediate dimer comprising primarily tri-substituted olefins instead of an intermediate dimer comprising primarily vinylidene olefins. Thus, use of an intermediate PAO dimer comprising primarily tri-substituted olefins is highly preferred over a dimer comprising primarily vinylidene due to the significant increases in yield of the $C_{28}$ co-dimer product that is commercially valuable for low viscosity applications.

Example 17

Example 17 was prepared in a manner identical to Example 15, except that the LAO feedstock in the second reactor for the acid based oligomerization was 1-decene instead of 1-octene. Applicants believe the dimer composition and other feedstocks used in Example 17 are also similar to the dimer composition and feedstocks used in multiple examples in U.S. Pat. No. 6,548,724. A sample was taken from the product stream of the second reactor and analyzed via GC, and the composition is provided below in Table 11.

Example 18

Example 18 was performed identical to Example 16, except that the LAO feedstock in the second reactor was 1-decene instead of 1-octene. A sample was taken from the product stream of the second reactor and analyzed. The overall composition of the reactor PAO product is provided below in Table 11. The $C_{30}$ fraction, prior to hydrogenation, has approximately 21% tetra-substituted olefins, as determined by carbon-NMR; the remaining structure is a mixture of vinylidene and tri-substituted olefins.

TABLE 11

| Second Reactor Effluent | Example 17 | Example 18 |
|---|---|---|
| Unreacted Monomer | 0.7% | 0.7% |
| Lighter Fractions | 7.3% | 9.0% |
| $C_{30}$ Fraction | 71.4% | 76.1% |
| Heavier Fractions | 20.6% | 14.2% |

Examples 17 and 18 show that, again, using a dimer intermediate comprising primarily tri-substituted olefins increases the yield of the desired $C_{30}$ product. Since the carbon number of the co-dimer and the $C_{10}$ trimer is the same in these experiments, it is infeasible to separately quantify the amount of co-dimer and $C_{10}$ trimer. Instead, the $C_{30}$ material was separated via distillation and the product properties were measured for both Examples 17 and 18.

For comparison purposes, a $C_{10}$ trimer was obtained from a $BF_3$ oligomerization wherein the above procedures for the second reactor of Examples 17 and 18 were used to obtain the trimer; i.e. there was no first reaction with either TNOA or Catalyst 1 and thus, no dimer feed element in the acid catalyst oligomerization. Properties of this $C_{10}$ trimer were measured and are summarized in Table 12 and compared to the $C_{30}$ trimers of Examples 17 and 18.

TABLE 12

| Example | KV at 100° C. (cSt) | KV at 40° C. (cSt) | VI | Pour Point (° C.) | Noack Volatility (%) |
|---|---|---|---|---|---|
| Example 17 $C_{30}$ | 3.47 | 14.1 | 127 | −69 | 13.9 |
| Example 18 $C_{30}$ | 3.50 | 14.1 | 130 | −78 | 12.0 |
| $BF_3$ $C_{10}$ trimer | 3.60 | 15.3 | 119 | −75 | 17.2 |

Table 12 evidences a clear difference between a $C_{30}$ material formed using a tri-substituted vinylene dimer feed element in a $BF_3$ oligomerization (Example 18) versus a $C_{30}$ material formed in a $BF_3$ oligomerization using a vinylidene dimer feed element (Example 17). The $C_{30}$ material obtained using tri-substituted vinylene dimers has a similar viscosity with a significantly improved VI and a lower Noack Volatility than the $C_{30}$ material obtained using vinylidene dimers under equivalent process conditions. Furthermore, the $C_{30}$ material obtained using vinylidene dimers has properties more similar to those of a $C_{10}$ trimer in a $BF_3$ process than the $C_{30}$ material obtained using tri-substituted vinylene dimers, indicating that a greater portion of the $C_{30}$ yield is a $C_{10}$ trimer and not a co-dimer of the vinylidene dimer and 1-decene.

What is claimed is:

1. A poly alpha olefin (PAO), wherein said PAO has a kinematic viscosity at 100° C. ($KV_{100}$) of less than 20 cSt and comprises dimer and trimer—wherein the dimer contains at least 25 wt % of tri-substituted vinylene olefins represented by the following structure:

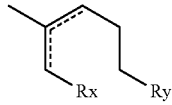

wherein the dashed line represents the two possible locations where the unsaturated double bond may be located and Rx and Ry are independently selected from a $C_3$ to $C_{21}$ alkyl group; and wherein the trimer of the PAO has a viscosity index (VI) of greater than 125.

2. The PAO of claim 1, wherein Rx and Ry are independently selected from a $C_3$ to $C_{11}$ alkyl group.

3. The PAO of claim 1, wherein the tri-substituted vinylene dimer is represented by the following structure:

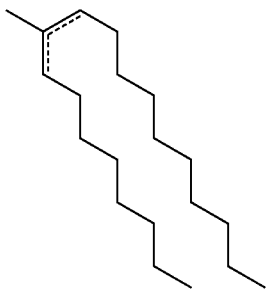

wherein the dashed line represents the two possible locations where the unsaturated double bond may be located.

4. The PAO of claim 1, wherein the PAO contains less than 70 wt % of di-substituted vinylidene represented by the following:

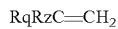

wherein Rq and Rz are independently selected from alkyl groups.

5. The PAO of claim 1, wherein the dimer portion of the PAO contains greater than 30 wt % of tri-substituted vinylene olefins.

6. The PAO of claim 1, wherein the dimer portion of the PAO contains from 25 to 80 wt % of tri-substituted vinylene olefins.

7. The PAO of claim 1, wherein the dimer portion of the PAO is a distillate effluent.

8. The PAO of claim 1, wherein the dimer portion of the PAO is a reactor effluent that has not been subjected to distillation.

9. The PAO of claim 1, wherein the PAO has not been subjected to a separate isomerization process following oligomerization.

10. The PAO of claim 1, wherein the trimer portion of the PAO has a Noack volatility of not greater than 14 wt %.

11. The PAO of claim 1 further comprising tetramers and higher oligomers, wherein the tetramers and higher oligomers portion of the PAO has a Noack volatility of not greater than 6 wt %.

12. The PAO of claim 1, wherein the trimer portion of the PAO after a hydrogenation step has a kinematic viscosity at 100° C. of less than 4 cSt.

13. The PAO of claim 1, wherein the trimer portion of the PAO after a hydrogenation step has a $KV_{100}$ of less than 3.6 cSt.

14. The PAO of claim 1 further comprising tetramers and higher oligomers, wherein the tetramers and higher oligomers portion of the PAO after a hydrogenation step has a $KV_{100}$ of less than 30 cSt.

15. The PAO of claim 1 consisting of the PAO dimer portion and a PAO oligomer portion remaining after the PAO dimer portion is removed, wherein the PAO oligomer portion remaining after the PAO dimer portion is removed has a $KV_{100}$ of less than 25 cSt.

16. The PAO of claim 1 which is made by oligomerization reaction from a feedstock, wherein the feedstock utilized in the oligomerization reaction is comprised of at least one linear alpha olefin wherein the linear alpha olefin is selected from at least one of 1-hexene, 1-octene, 1-nonene, 1-decene, 1-dodecene, 1-tetradecene, and combinations thereof.

17. The PAO of claim 1, when prepared by a process comprising oligomerizing one or more $C_6$ to $C_{14}$ linear alpha olefins in the presence of a metallocene oligomerization catalyst.

* * * * *